United States Patent
Fukami et al.

(10) Patent No.: US 10,073,014 B2
(45) Date of Patent: Sep. 11, 2018

(54) EXHAUST GAS SAMPLING MECHANISM AND EXHAUST GAS ANALYSIS APPARATUS

(71) Applicant: HORIBA, Ltd., Kyoto (JP)

(72) Inventors: Shun Fukami, Kyoto (JP); Yoshihisa Onda, Kyoto (JP); Kazuo Hanada, Kyoto (JP)

(73) Assignee: Horiba Ltd., Kyoto (JP)

( * ) Notice: Subject to any disclaimer, the term of this patent is extended or adjusted under 35 U.S.C. 154(b) by 46 days.

(21) Appl. No.: 14/713,905

(22) Filed: May 15, 2015

(65) Prior Publication Data

US 2015/0330875 A1    Nov. 19, 2015

(30) Foreign Application Priority Data

May 16, 2014    (JP) ................... 2014-102290

(51) Int. Cl.
*G01N 1/22*    (2006.01)
*G01M 15/10*   (2006.01)

(52) U.S. Cl.
CPC ........ *G01N 1/2205* (2013.01); *G01M 15/102* (2013.01); *G01N 1/2247* (2013.01); *G01N 1/2252* (2013.01); *G01N 1/2258* (2013.01)

(58) Field of Classification Search
CPC .. G01N 1/2205; G01N 1/2247; G01N 1/2252; G01N 1/2258; G01M 15/102
USPC ..................................... 73/863.23
See application file for complete search history.

(56) References Cited

U.S. PATENT DOCUMENTS

| | | | | |
|---|---|---|---|---|
| 3,961,896 A | * | 6/1976 | Dunn | ................. G01N 33/0013 |
| | | | | 422/90 |
| 5,173,263 A | | 12/1992 | Lee | |
| 5,762,771 A | * | 6/1998 | Yamada | ............... G01N 27/407 |
| | | | | 204/427 |
| 5,782,230 A | * | 7/1998 | Linnebur | ............ A47J 37/0713 |
| | | | | 126/38 |
| 7,497,138 B2 | * | 3/2009 | Kubinski | .............. F01N 13/008 |
| | | | | 73/114.71 |

(Continued)

FOREIGN PATENT DOCUMENTS

| | | |
|---|---|---|
| CN | 102192930 A | 9/2011 |
| CN | 102472694 A | 5/2012 |
| EP | 0244936 A1 | 11/1987 |

OTHER PUBLICATIONS

EESR dated Sep. 21, 2015 issued for European patent application No. 15 167 508.9, 7 pgs.

(Continued)

*Primary Examiner* — Natalie Huls
*Assistant Examiner* — Monica S Young
(74) *Attorney, Agent, or Firm* — Brooks Kushman P.C.

(57) ABSTRACT

To provide an exhaust gas sampling mechanism which can prevent condensed water droplets in exhaust gas from being sampled by a sampling probe and advantageously sample only the gas components of the exhaust gas to be measured, thereby maintaining a high response speed in analyzing the exhaust gas, the exhaust gas sampling mechanism includes the sampling probe disposed in a flow path through which the exhaust gas flows, for sampling the exhaust gas; and a gas-permeable cover which covers at least an upstream portion or a lateral surface portion of the sampling probe in the flow path, and has a water droplet removing structure.

5 Claims, 7 Drawing Sheets

(a)

(b)

(56) References Cited

U.S. PATENT DOCUMENTS

| | | | |
|---|---|---|---|
| 8,087,308 B2 | 1/2012 | Gauthier et al. | |
| 2005/0257605 A1* | 11/2005 | Colvin | G01F 1/88 |
| | | | 73/114.76 |
| 2006/0065541 A1* | 3/2006 | Nishio | G01N 27/4077 |
| | | | 205/427 |
| 2008/0175759 A1 | 7/2008 | Oishi et al. | |
| 2010/0199787 A1* | 8/2010 | Gauthier | G01N 1/2258 |
| | | | 73/863.23 |
| 2011/0174052 A1 | 7/2011 | Kuebel | |
| 2013/0031952 A1* | 2/2013 | Day | G01N 27/4077 |
| | | | 73/23.31 |
| 2015/0047330 A1* | 2/2015 | Zhang | F01N 3/02 |
| | | | 60/311 |

OTHER PUBLICATIONS

Office Action dated Jul. 18, 2018 issued for Chinese Patent Application No. 201510241247.7, 9 pgs.

* cited by examiner (a)

(b)

10,073,014 B2

EXHAUST GAS SAMPLING MECHANISM AND EXHAUST GAS ANALYSIS APPARATUS

CROSS-REFERENCE TO RELATED APPLICATION

This application claims priority to JP Application No. 2014-102290, filed May 16, 2014, the disclosure of which is incorporated in its entirety by reference herein.

TECHNICAL FIELD

The present invention relates to an exhaust gas sampling mechanism for sampling exhaust gas from a flow path through which the exhaust gas flows.

BACKGROUND

An exhaust gas sampling mechanism has partially sampled exhaust gas flowing through a flow path such as an exhaust pipe, and the exhaust gas has been led into an exhaust gas analysis apparatus for analyzing exhaust gas components such as carbon monoxide (CO), carbon dioxide ($CO_2$), nitrogen oxide (NOX), and total hydrocarbon (THC).

As FIG. 7 illustrates, the exhaust gas sampling mechanism 3A includes an attachment pipe 31A, a sampling probe 32A, and a protection pipe 34A (See U.S. Pat. No. 8,087, 308). The attachment pipe 31A is attached to the open end of the exhaust pipe of a vehicle. The sampling probe 32A is inserted from the lateral surface of the attachment pipe 31A into the attachment pipe 31A. The protection pipe 34A has a substantially cylindrical shape, and covers the periphery of the sampling probe 32A in the flow path.

Only the downstream surface of the protection pipe 34A has an opening in a flow path through which exhaust gas flows. The exhaust gas enters the protection pipe 34A through the opening on the downstream side, and the entered exhaust gas is sampled by the sampling probe 32A. This configuration prevents solid components such as ash and dusts in the exhaust gas from entering the sampling probe 32A from the upstream surface of the protection pipe 34A, thereby preventing a malfunction such as clogging in the sampling probe 32A.

However, in the above configuration of the protection pipe 34A, when condensed water droplets in the exhaust gas come to the protection pipe 34A, the condensed water droplets may enter and be accumulated in the protection pipe 34A. When, for example, water W accumulated at the bottom of the inside of the protection pipe 34A evaporates, the concentration of water in the exhaust gas becomes abnormally higher than the normal concentration of water. This may adversely affect not only the measurement of the concentration of water but also the measurement accuracy of other exhaust gas components due to water interference and others. Moreover, as FIG. 6 illustrates, the protection pipe 34A has the opening into which the exhaust gas flows in the direction opposite the direction in which the whole exhaust gas flows. Therefore, it is difficult for the exhaust gas to enter the protection pipe 34A, which leads a decrease in response speed in analysis by an exhaust gas analysis apparatus.

SUMMARY

Technical Problem

In view of the above problems, the present invention provides an exhaust gas sampling mechanism which can prevent condensed water droplets in exhaust gas from being sampled by a sampling probe and advantageously sample only the gas components of the exhaust gas to be measured, thereby maintaining a high response speed in analyzing the exhaust gas.

Solution to Problem

That is, the exhaust gas sampling mechanism according to the present invention includes: a sampling probe disposed in a flow path through which exhaust gas flows, for sampling the exhaust gas; and a gas-permeable cover which covers at least an upstream portion or a lateral surface portion of the sampling probe in the flow path, and has a water droplet removing structure.

This configuration allows the gas-permeable cover having the water droplet removing structure to remove condensed water droplets by the water adhering thereto, and allows the sampling probe to sample only the gas components of the exhaust gas which have passed through the gas-permeable cover. This can eliminate adverse effects on the accuracy of each measurement due to water droplets in the exhaust gas. Moreover, the gas components of the exhaust gas can pass through the gas-permeable cover provided upstream from the sampling probe. Therefore, a large amount of exhaust gas is easily led into the sampling probe, thereby increasing a response speed in analyzing the exhaust gas.

The gas-permeable cover may be formed with a metal mesh or a metal plate having holes to make it difficult for small-diameter water droplets in the exhaust gas to pass through the gas-permeable cover. In such a gas-permeable cover, the lattice of the metal mesh functions as the water droplet removing structure for removing water droplets from the exhaust gas by the water adhering thereto. The openings of the metal mesh function as a gas-permeable structure which the gas components of the exhaust gas pass through. Accordingly, the gas components of the exhaust gas can be efficiently sampled by the sampling probe while the water is removed from the exhaust gas.

When the water droplets in the exhaust gas stick to and block the gas-permeable structure in the gas-permeable cover, it is difficult for the gas components of the exhaust gas to pass through the gas-permeable structure. To prevent the situation while preventing the water droplets from passing through the gas-permeable structure, the gas-permeable cover may be formed with a metal mesh having a size of larger than 50 mesh and smaller than 200 mesh.

The gas-permeable cover formed with a metal mesh having a size of 100 mesh is a specific embodiment for advantageously collecting water droplets in the exhaust gas by the gas-permeable cover.

The gas-permeable cover may be provided to cover a semi-cylindrical upstream portion of the sampling probe to prevent the water removed by the gas-permeable cover from being accumulated near the sampling probe and to allow the sampling probe to advantageously sample only the gas components of the exhaust gas. When this kind of gas-permeable cover is used, the gas-permeable cover has a semi-cylindrical shape. Therefore, the water collected by the gas-permeable cover is discharged from the openings of the gas-permeable cover to the outside. In particular, when the axial directions of the sampling probe and the gas-permeable cover are the same direction as the horizontal direction, a concave portion where water droplets are accumulated is not present in the inside of the gas-permeable cover. Accordingly, the collected water can be efficiently discharged to the outside of the gas-permeable cover.

Advantageous Effects

According to the exhaust gas sampling mechanism in the present invention, the gas-permeable cover having the water droplet removing structure is provided at least upstream from the sampling probe or a part of the lateral surface portion of the sampling probe. Therefore, exhaust gas can be analyzed at a high response speed by allowing only gas components suitable for exhaust gas analysis to pass through the gas-permeable cover in a large amount while collecting water droplets in the exhaust gas with the gas-permeable cover.

DESCRIPTION OF EMBODIMENTS

The following describes an exhaust gas sampling mechanism 3 and an exhaust gas analysis system 200 according to an embodiment of the present invention with reference to the drawings.

Figure 1:
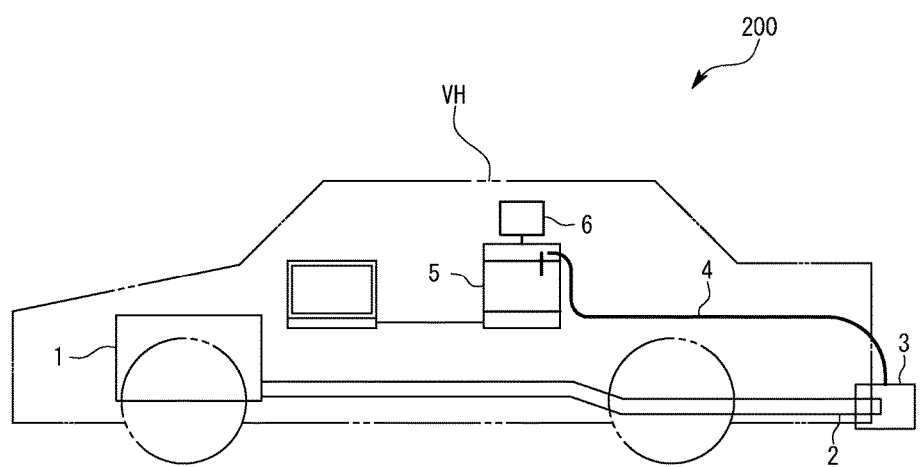
FIG. 1 is a schematic view illustrating an exhaust gas sampling mechanism and an exhaust gas analysis system according to an embodiment of the present invention.

The exhaust gas analysis system 200 according to the present embodiment is an onboard system, and analyzes the components of exhaust gas emitted from an exhaust pipe 2 connected to an internal combustion engine 1 (engine) of a vehicle VH as FIG. 1 illustrates. The components are, for example, carbon monoxide (CO), carbon dioxide (CO2), nitrogen oxide (NOX), and total hydrocarbon (THC). Here, the analysis is a concept including, for example, the detection of the presence of target substances to be analyzed and the measurement of the concentration of each substance.

Specifically, the exhaust gas analysis system 200 includes, as FIG. 1 illustrates, the exhaust gas sampling mechanism 3, an exhaust gas analysis apparatus 5, a hot hose 4, and a power supply switching apparatus 6. The exhaust gas sampling mechanism 3 is attached to the end portion of the opening side of the exhaust pipe 2. The exhaust gas analysis apparatus 5 is installed in the vehicle. The hot hose 4 leads exhaust gas sampled by the exhaust gas sampling mechanism 3 to the exhaust gas analysis apparatus 5 at a predetermined temperature. The power supply switching apparatus 6 supplies power to the exhaust gas analysis apparatus 5.

The exhaust gas analysis apparatus 5 analyzes the concentration of CO and the concentration of CO2 in the exhaust gas with a non-dispersive infrared (NDIR) absorption method, and analyzes the concentration of NOX in the exhaust gas with a chemiluminescence method or a non-dispersive ultraviolet (NDUV) analysis method. Moreover, the exhaust gas analysis apparatus 5 analyzes the concentration of THC in the exhaust gas with a flame ionization detection (FID) method. For instance, when condensed water droplets in the sampled exhaust gas evaporate and the concentration of water of the exhaust gas excessively increases, the accuracy of the analysis with the NDIR absorption method may be adversely affected. Therefore, in the present embodiment, water droplets in the exhaust gas flowing through the exhaust pipe 2 are prevented from being sampled by the exhaust gas sampling mechanism 3.

Figure 2:
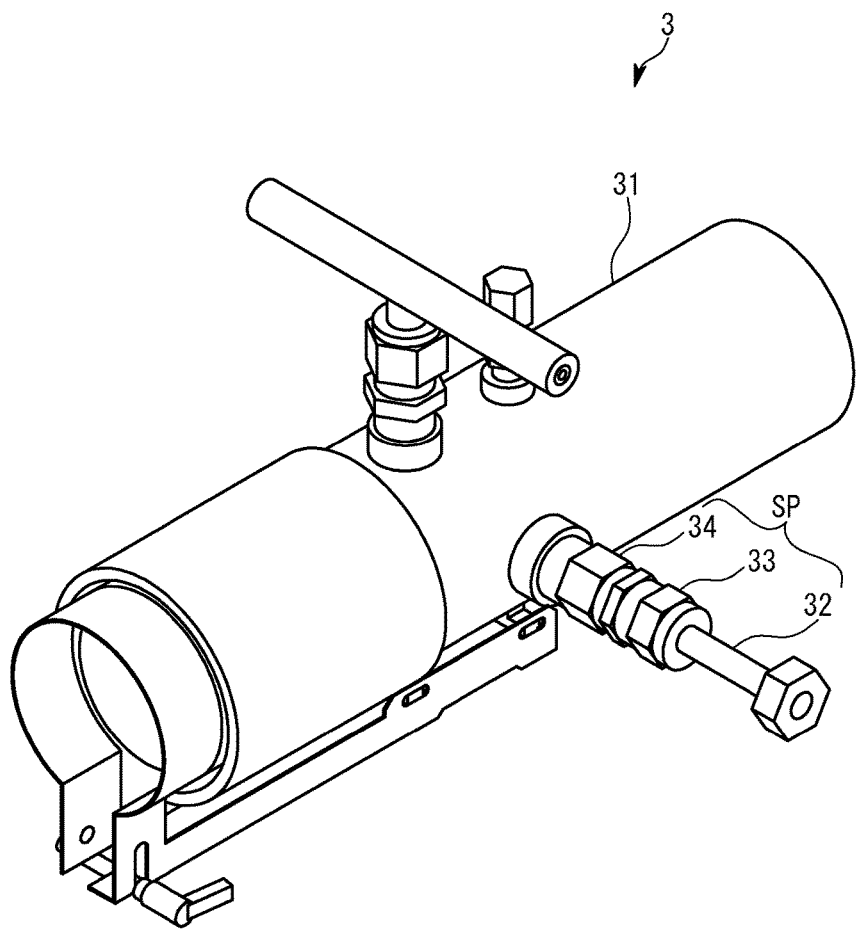
FIG. 2 is a schematic perspective view illustrating the exhaust gas sampling mechanism in the embodiment.
Figure 3:
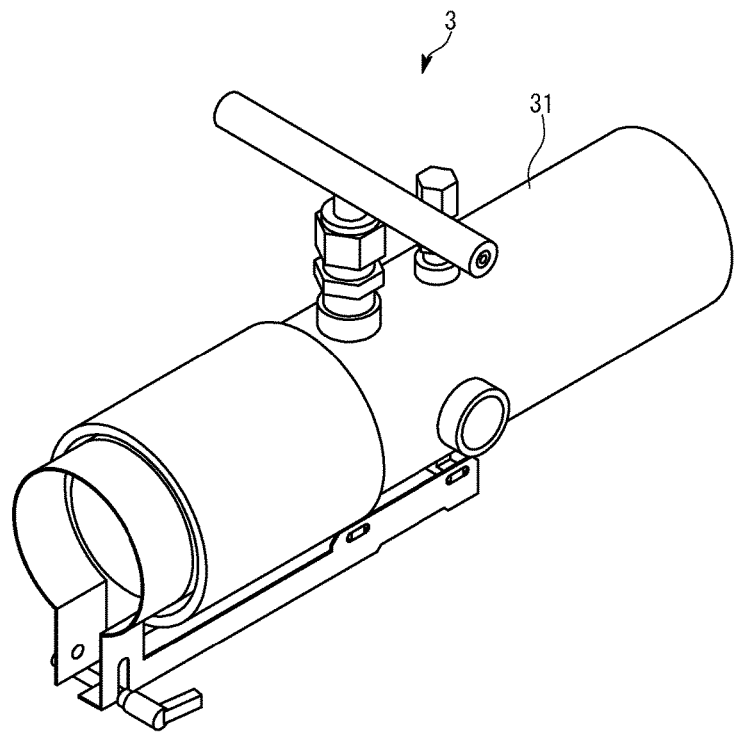
FIG. 3 is a schematic exploded perspective view of the exhaust gas sampling mechanism in the embodiment.
Figure 3:
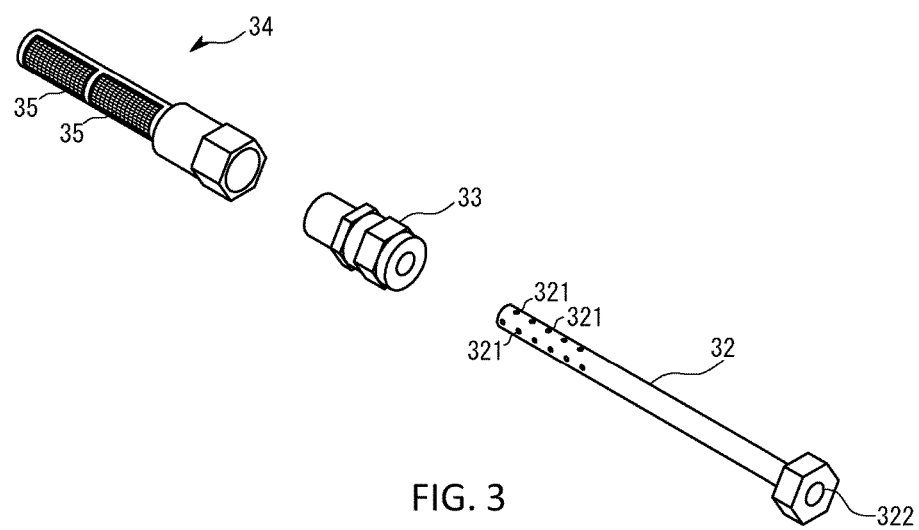
Figure 4:
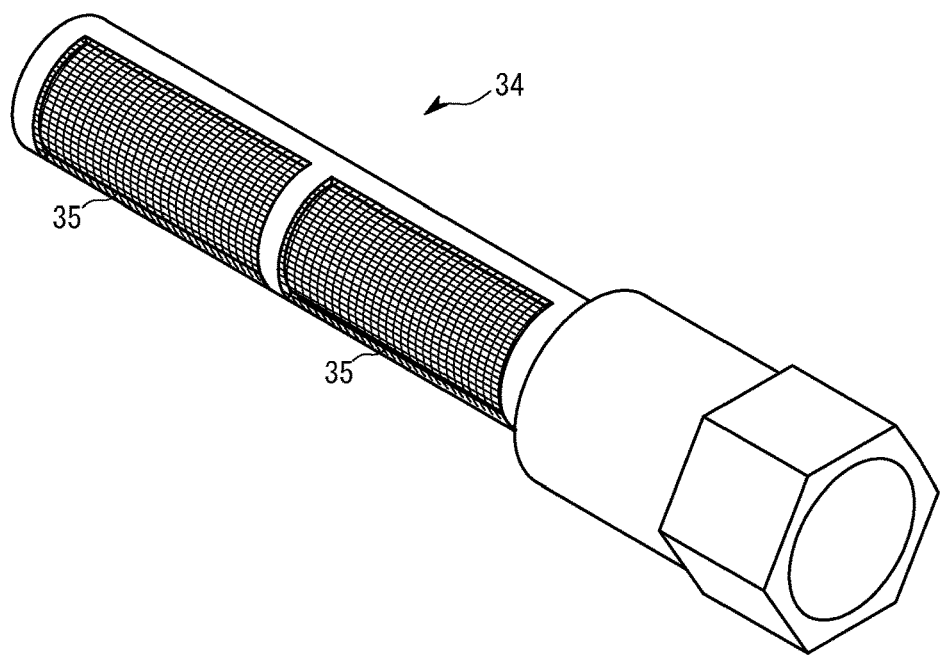
FIG. 4 is a schematic enlarged perspective view illustrating in detail a protection pipe and a gas-permeable cover in the embodiment.
Figure 4:
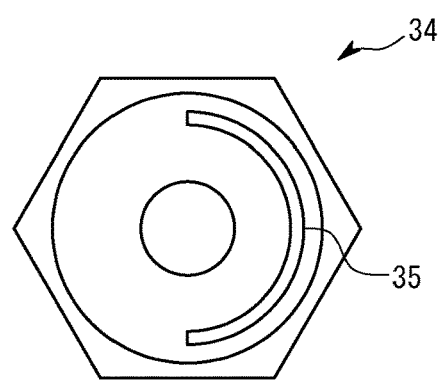

The following describes in detail the exhaust gas sampling mechanism 3 with reference to FIGS. 2 to 4.

As FIG. 2 illustrates, the exhaust gas sampling mechanism 3 includes an attachment pipe 31 and an exhaust gas sampling pipe SP. The attachment pipe 31 has a substantially cylindrical shape, and is attached to the end portion of the opening side of the exhaust pipe 2 in the same axial direction as the exhaust pipe 2. The exhaust gas sampling pipe SP is inserted from an insertion opening of the lateral surface of the attachment pipe 31 into the attachment pipe 31. That is, as FIGS. 2 and 3 illustrate, the exhaust gas sampling pipe SP is attached to the attachment pipe 31 so that the axial direction of the exhaust gas sampling pipe SP is the horizontal direction.

As FIG. 3 illustrates, the exhaust gas sampling pipe SP includes a sampling probe 32, a protection pipe 34, and a joint 33. In the attachment pipe 31, the protection pipe 34 covers the outer peripheral surface of the sampling probe 32 at a certain distance therebetween. The joint 33 is provided between the sampling probe 32 and the protection pipe 34.

The sampling probe 32 is disposed in a flow path through which the exhaust gas flows from the exhaust pipe into the attachment pipe 31, and partially samples the exhaust gas from the flow path. As FIG. 3 illustrates, the sampling probe 32 has a substantially slender hollow cylindrical shape, and the side surface of an end portion of the sampling probe 32 has many small-diameter exhaust gas sampling inlets 321. The base end of the sampling probe 32 is connected to the hot hose 4. An exhaust gas outlet 322 from which the sampled exhaust gas is led into the hot hose 4 is formed at the base end.

As is clear from FIG. 3, (a) in FIG. 4, and (b) in FIG. 4, the protection pipe 34 has a hollow semi-cylindrical shape and a larger diameter than the sampling probe 32. The assembled protection pipe 34 and sampling probe 32 have a double-pipe structure. It should be noted that (b) in FIG. 4 is a schematic view illustrating one end of the protection pipe 34 viewed along the horizontal direction. Moreover, when the protection pipe 34 is viewed in the horizontal direction, the direction of the apex of the semicircle is opposite the direction in which the exhaust gas flows, thereby preventing water from being accumulated in the inner peripheral surface of the protection pipe 34. Furthermore, gas-permeable covers 35 formed into mesh form a part of a semi-cylindrical area which is the upstream surface of the protection pipe 34 in the flow path through which the exhaust gas flows. The gas-permeable covers 35 are held by a semi-cylindrical holder having openings on the side thereof.

As (a) in FIG. 4 illustrates, the gas-permeable cover 35 is formed with a metal mesh bent into a semi-cylindrical shape in the present embodiment. The gas-permeable covers 35 are disposed to entirely cover the upstream portion of the sampling probe 32. The lattice of the metal mesh functions as a water droplet removing structure for removing water droplets from the exhaust gas by the water adhering thereto. Meanwhile, the openings of the metal mesh function as a gas-permeable structure which the gas components of the exhaust gas pass through. The metal mesh forming the gas-permeable cover 35 has a mesh size of larger than 50 mesh and smaller than 200 mesh. In the present embodiment, a metal mesh having a size of 100 mesh is used. Here, "mesh" means mesh count per 1 inch.

It should be noted that at the mesh size of the metal mesh forming the gas-permeable cover 35, condensed water droplets in the exhaust gas are collected at the lattice, but the collected water droplets do not block the meshes of the metal mesh.

According to the exhaust gas sampling mechanism 3 and the exhaust gas analysis system 200, the gas-permeable cover 35 formed with a metal mesh covers the exhaust gas inlets 321 of the sampling probe 32 on the upstream side. This allows the lattice of the metal mesh to remove not only solid components such as a dust but also water droplets from the exhaust gas passing through the gas-permeable cover 35. The exhaust gas will then enter the protection pipe 34. Accordingly, only the gas components of the exhaust gas enter the protection pipe 34.

Moreover, the protection pipe 34 has a semi-cylindrical shape, and is disposed so that a portion where the water droplets removed by the gas-permeable cover 35 are received is not present in the inner peripheral surface of the protection pipe 34, thereby discharging the removed water from the opening of the protection pipe 34 to the outside. Therefore, unlike the conventional type, water droplets are not accumulated near the sampling probe 32, and exhaust gas of abnormally high water concentration is not sampled.

That is, unlike the conventional type, condensed water droplets in the exhaust gas do not enter and are not accumulated in the protection pipe 34. This can prevent the water droplets in the exhaust gas from adversely affecting each measurement performed by the exhaust gas analysis apparatus.

Moreover, the gas-permeable covers 35 are formed on the upstream surface of the protection pipe 34, so that the exhaust gas can pass through the gas-permeable covers 35 and reach the sampling probe 32 in the original flow direction. This means that the gas components of the exhaust gas are easily led into the protection pipe 34. Therefore, the exhaust gas analysis apparatus can analyze the exhaust gas, maintaining a high response speed. Besides, if the gas-permeable cover 35 is soiled with, for example, ash in the exhaust gas and gas permeability decreases, a gas-permeable function can be easily recovered by replacing or washing only the soiled gas-permeable cover 35.

Furthermore, the protection pipes 34 in various shapes can be attached with the joint 33 according to the measurement of the exhaust gas. For instance, an appropriate protection pipe can be attached according to an exhaust gas condition by preparing the protection pipes 34 having differences in places where the gas-permeable covers 35 are provided or in the mesh sizes of the metal meshes. This can achieve more preferable sampling of exhaust gas even if, for example, the amount of water droplets in emitted exhaust gas is different according to whether the internal combustion engine 1 is a gasoline engine or a diesel engine. It should be noted that in some cases, the sampling probe 32 can be directly disposed in the flow path without the protection pipe 34.

Figure 5:
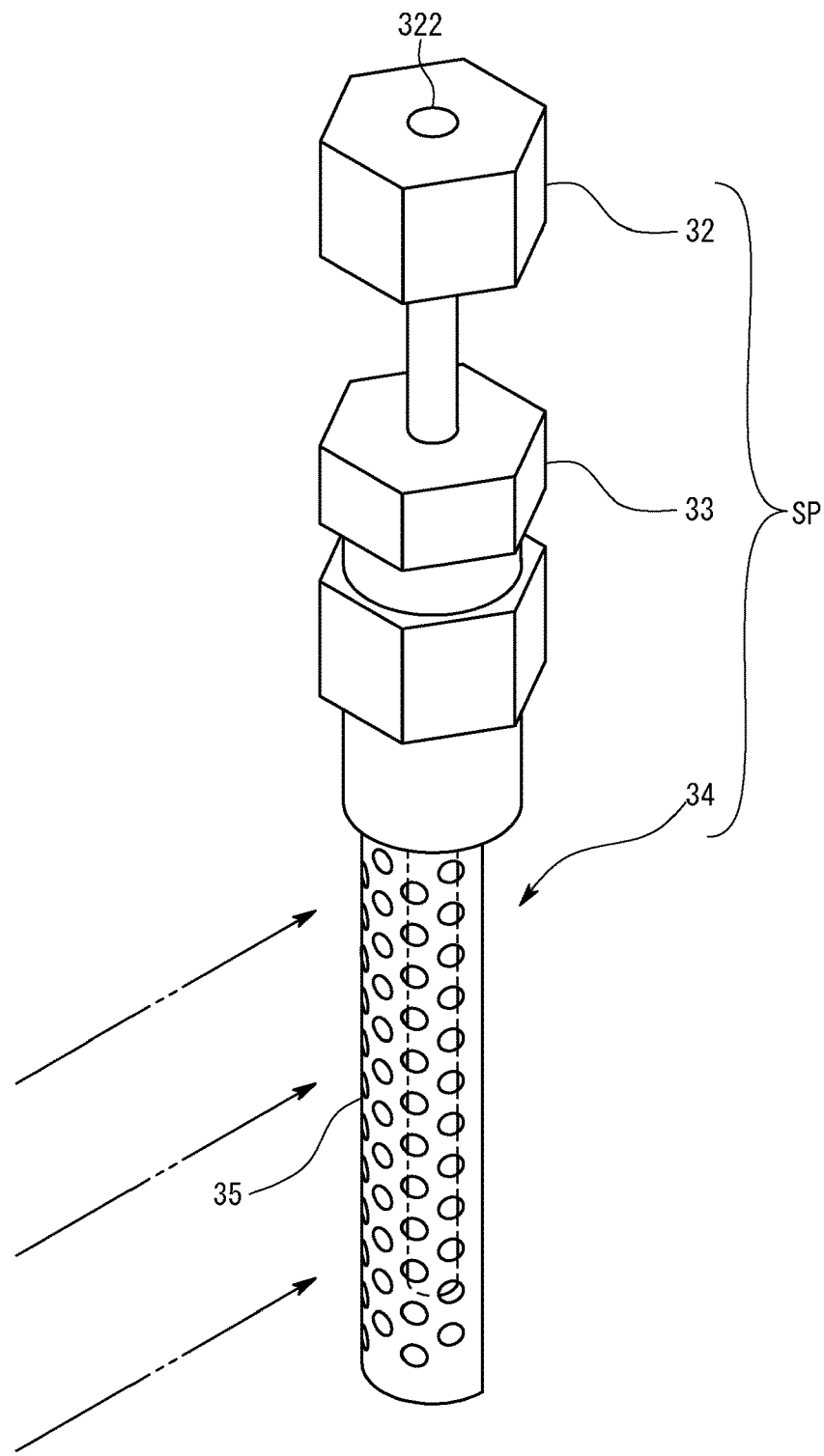
FIG. 5 is a schematic perspective view illustrating an example of the gas-permeable cover of an exhaust gas sampling mechanism according to another embodiment of the present invention.

The following describes an exhaust gas sampling mechanism according to another embodiment of the present invention with reference to FIG. 5. It should be noted that the identical reference signs are hereinafter used to designate components corresponding to the components in the above embodiment.

The protection pipe 34 in the present embodiment is set to the attachment pipe 31 so that the axial direction of the protection pipe 34 is the vertical direction. The protection pipe 34 is a metal plate having holes, and is made of only the gas-permeable cover 35 which is a perforated metal formed into mesh (punching mesh). Moreover, the protection pipe 34 has a semi-cylindrical shape, and does not cover the entire periphery of the sampling probe 32, but covers only the upstream portion of the sampling probe 32. Many through holes are formed by punching, across substantially the entire surface of the semi-cylindrical protection pipe 34. While water droplets in exhaust gas are collected at the lattice of the protection pipe 34, the gas components of the exhaust gas pass through the through holes. That is, in the present embodiment, while the through holes of the punching metal function as the gas-permeable structure, the rest of the plate (lattice) functions as the water droplet removing structure.

It should be noted that the diameters or density of the through holes of the punching metal may be set to values corresponding to the mesh sizes described in the above embodiment. For instance, a punching metal may be used which has through holes whose diameters, density, or opening ratio corresponds to the diameters, density, or opening ratio of through holes in 50 to 200 mesh.

Even this kind of punching metal can advantageously prevent condensed water droplets in the exhaust gas from being sampled by the sampling probe 32, and maintain high measurement accuracy of the components of the exhaust gas, in the same manner as the above embodiment.

The following describes other embodiment.

In the above embodiments, the gas-permeable covers 35 are provided only upstream from the sampling probe 32. However, for example, the gas-permeable covers 35 may be provided to cover the entire periphery of the sampling probe 32. Moreover, the gas-permeable covers 35 may cover, for example, only a ¼ of the cylindrical sampling probe 32 on the upstream side as well as the semi-cylindrical portion of the sampling probe 32. That is, the gas-permeable cover 35 may cover at least the upstream portion of the sampling probe 32 to prevent condensed water droplets in the exhaust gas from directly entering the sampling probe 32 or to reduce water droplets which will enter the sampling probe 32.

Figure 7:
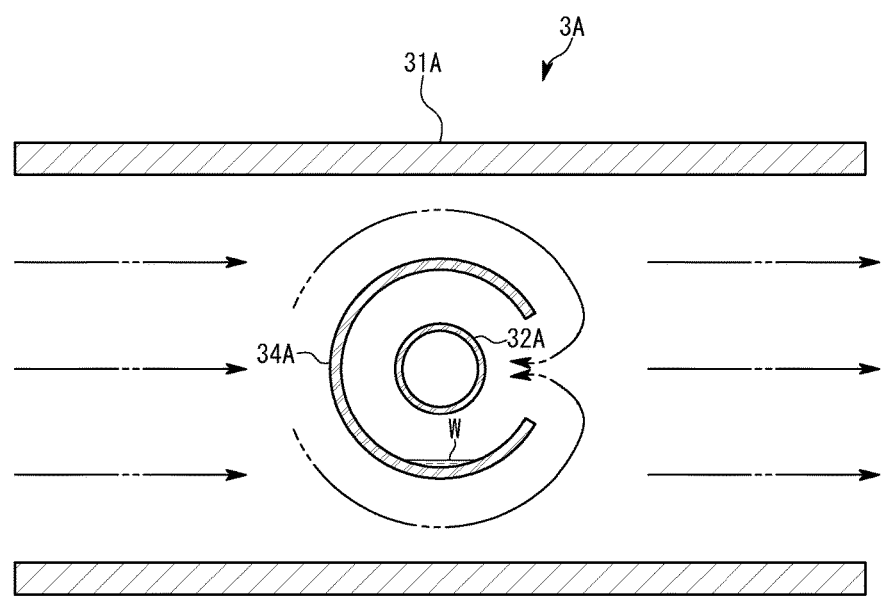
FIG. 7 is a schematic view illustrating a conventional exhaust gas sampling mechanism.

To prevent water droplets removed by the gas-permeable covers 35 from being accumulated near the sampling probe 32, the protection pipe 34 may be, for example, a partial cylindrical protection pipe having an opening which is formed by cutting a portion of the side of the protection pipe 34 in the axial direction. Moreover, the orientation of the protection pipe 34 is set so that an open end of the side of the protection pipe 34 is at the lowest position in the vertical direction. By so doing, it is easier to discharge by gravity removed water to the outside of the protection pipe 34. More specifically, the orientation of the protection pipe 34 is set so that the virtual horizontal plane which passes the open end of the side of the protection pipe does not interest with other parts of the protection pipe 34. By so doing, the water accumulation portion as FIG. 7 illustrates is not formed, and removed water can be promptly discharged to the outside of the protection pipe 34.

A metal mesh forming the gas-permeable cover 35 may be selected based on not only mesh representing a mesh size but also, for example, the diameter or the size of an opening.

In the above embodiments, the exhaust gas sampling mechanism 3 for sampling exhaust gas from a flow path is employed in the onboard exhaust gas analysis system 200. However, the present invention may be applied to an exhaust gas analysis system which is not intended to be installed in a vehicle, for example. Moreover, the exhaust gas sampling mechanism 3 in the present invention may be used for sampling exhaust gas from a flow path when an internal combustion engine is solely evaluated.

The exhaust gas sampling mechanism 3 that has the attachment pipe 31, the sampling probe 32, and the protection pipe 34 is not limited the one as illustrated by FIG. 2: the attachment pipe 31 has the substantially cylindrical shape and is attached to the exhaust pipe 2 along to an axial direction, the sampling probe 32 and the protection pipe 34 are perpendicularly inserted from the lateral surface of the attachment pipe 31. For example, the sampling probe 32 may be inserted inside of the exhaust pipe 2 so that each axial direction of the sampling probe 32 and the exhaust pipe 2 matches, and the gas-permeable cover 35 may be provided to the upstream portion of the end portion of the sampling probe 32. This is because the gas-permeable cover 35 works if the gas-permeable cover 35 is covers at least the upstream portion of the sampling probe 32. Thus the gas-permeable cover 35 is not limited the one that covers the upstream portion from the lateral surface of the sampling probe 32, but the gas-permeable cover 35 may be provided to the upstream portion from an apical surface of the sampling probe 32. Thus the position of the gas-permeable cover 35 may change according to a direction of the sampling probe 32 in the flow path through which exhaust gas flows.

Even this kind of the exhaust gas sampling mechanism 3 can produce effects as the above embodiments. Thus, the gas-permeable cover 35 can remove the water droplet from the exhaust gas, and the sampling probe 32 can sample almost exclusively the gas component of the exhaust gas. Therefore, reliability of the analysis can be maintained.

Figure 6:
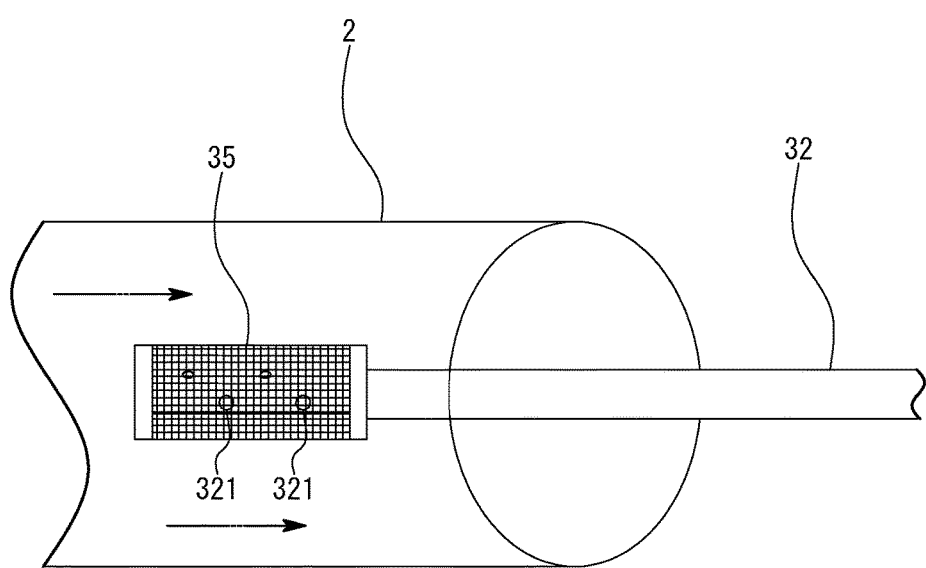
FIG. 6 is a schematic view illustrating an exhaust gas sampling mechanism according to yet another embodiment of the present invention.

In addition, the sampling probe 32 may be inserted directly inside of the exhaust pipe 2 without using attachment pipe 31. Even though the sampling probe 32 that is provided as stated before, the sampling probe 32 can sample almost exclusively the gas component of the exhaust gas by the gas-permeable cover 35 that has the water droplet removing structure: the gas permeable cover 35 is provided so as to cover at least of the lateral surface that has the exhaust gas sampling inlets 321 at the end portion of the sampling probe 32 and to remove the water droplet from the exhaust gas as illustrated in FIG. 6, As described above, in the flow of the exhaust gas that arrives inside of the sampling probe 32, the gas-permeable cover 35 may be provided to the upstream side of the sampling probe 32.

Without departing from the scope of the present invention, the embodiments may be variously modified or combined.

REFERENCE SIGNS LIST 200 exhaust gas analysis system
3 exhaust gas sampling mechanism
31 attachment pipe
32 sampling probe
33 joint
34 protection pipe
35 gas-permeable cover
1 internal combustion engine
2 exhaust pipe
4 hot hose
5 exhaust gas analysis apparatus
6 power supply switching apparatus

What is claimed is:

1. A exhaust gas sampling mechanism that is inserted to an attachment pipe attached to an exhaust pipe, the exhaust gas sampling mechanism comprising:
    a sampling probe disposed in a flow path through which exhaust gas flows and configured to sample the exhaust gas; and
    an unshielded metal mesh cover forming a semi-cylindrical protection pipe around a portion of the sampling probe without completely surrounding the sampling probe and without any intervening members between the metal mesh cover and sampling probe, spaced away from an outer surface of the sampling probe, and defining a plurality of openings such that the cover permits passage of the exhaust gas therethrough and promotes adherence of water from the exhaust gas thereon resulting in formation of droplets to remove water from the exhaust gas, wherein the cover is shaped and oriented to promote flow of the droplets toward at least one peripheral edge of the cover to discharge the droplets and preclude pooling of the droplets underneath the sampling probe between the sampling probe and cover.

2. The exhaust gas sampling mechanism according to claim 1, wherein the cover is a metal mesh having a size of larger than 50 mesh and smaller than 200 mesh.

3. The exhaust gas sampling mechanism according to claim 1, wherein the cover is a metal mesh having a size of 100 mesh.

4. An exhaust gas analysis system comprising:
    an exhaust gas analysis apparatus configured to analyze components of exhaust gas; and
    an exhaust gas sampling mechanism configured to supply exhaust gas to the exhaust gas analysis apparatus, inserted to an attachment pipe attached to an exhaust pipe, and including
        a sampling probe disposed in a flow path through Which the exhaust gas flows and configured to sample the exhaust gas, and
        an unshielded metal mesh cover forming a semi-cylindrical protection pipe around a portion of the sampling probe without completely surrounding the sampling probe and without any intervening members between the metal mesh cover and sampling probe, spaced away from an outer Surface of the sampling probe, and defining a plurality of openings such that the cover permits passage of the exhaust gas therethrough and promotes adherence of water from the exhaust gas thereon resulting in formation of droplets to remove water from the exhaust gas, wherein the cover is shaped and oriented to promote flow of the droplets toward at least one peripheral edge of the cover to discharge the droplets and preclude pooling of the droplets underneath the sampling probe between the sampling probe and cover.

5. An exhaust gas sampling mechanism that is inserted to an attachment pipe attached to an exhaust pipe, the exhaust gas sampling mechanism comprising:

a sampling probe disposed in a flow path through which exhaust gas flows and configured to sample the exhaust gas; and an unshielded metal plate cover forming a semi-cylindrical protection pipe around a portion of the sampling probe without completely surrounding the sampling probe and without any intervening members between the metal plate cover and sampling probe, spaced away from an outer surface of the sampling probe, and defining a plurality of openings such that the cover permits passage of the exhaust gas therethrough and promotes adherence of water from the exhaust gas thereon resulting in formation of droplets to remove water from the exhaust gas, wherein the cover is shaped and oriented to promote flow of the droplets toward at least one peripheral edge of the cover to discharge the droplets and preclude pooling of the droplets underneath the sampling probe between the sampling probe and cover.

* * * * *